US006659611B2

(12) United States Patent
Amir et al.

(10) Patent No.: US 6,659,611 B2
(45) Date of Patent: Dec. 9, 2003

(54) SYSTEM AND METHOD FOR EYE GAZE TRACKING USING CORNEAL IMAGE MAPPING

(75) Inventors: Arnon Amir, Saratoga, CA (US); Myron Dale Flickner, San Jose, CA (US); David Bruce Koons, San Jose, CA (US); Carlos Hitoshi Morimoto, Sao Paulo (BR)

(73) Assignee: International Business Machines Corporation, Armonk, NY (US)

( * ) Notice: Subject to any disclaimer, the term of this patent is extended or adjusted under 35 U.S.C. 154(b) by 116 days.

(21) Appl. No.: 10/034,524

(22) Filed: Dec. 28, 2001

(65) Prior Publication Data
US 2003/0123027 A1 Jul. 3, 2003

(51) Int. Cl.[7] .................................. A61B 3/14

(52) U.S. Cl. ..................................... 351/210

(58) Field of Search ............... 351/209, 210, 351/208, 200, 205, 206, 211, 221; 382/103, 291; 708/141; 702/151

(56) References Cited
U.S. PATENT DOCUMENTS

| 4,597,648 | A | | 7/1986 | Feldon et al. ............. 351/212 |
|---|---|---|---|---|
| 4,836,670 | A | * | 6/1989 | Hutchinson .............. 351/210 |
| 5,231,674 | A | | 7/1993 | Cleveland et al. ........... 382/6 |
| 5,270,748 | A | * | 12/1993 | Katz .......................... 351/210 |
| 5,325,133 | A | | 6/1994 | Adachi ....................... 351/209 |
| 5,331,149 | A | | 7/1994 | Spitzer et al. .............. 250/221 |
| 5,481,622 | A | * | 1/1996 | Gerhardt et al. ........... 382/103 |
| 5,644,642 | A | | 7/1997 | Kirschbaum .............. 382/103 |
| 6,061,084 | A | | 5/2000 | Perlin ........................ 348/51 |
| 6,152,563 | A | * | 11/2000 | Hutchinson et al. ........ 351/209 |
| 6,204,828 | B1 | | 3/2001 | Amir et al. ................. 345/7 |

FOREIGN PATENT DOCUMENTS

| EP | 631222 | 12/1994 | ............ G06F/3/00 |
|---|---|---|---|
| WO | WO9926126 | 5/1999 | ............ G06F/3/00 |

OTHER PUBLICATIONS

K. Talmi and J. Liu, "Eye and Gaze Tracking for Visually Controlled Interactive Stereoscopic Displays", Image Communication, vol. 14, No. 10, p. 799–810, 1999.

S. Shih, Y. Wu, J. Liu, "A Calibration–Free Gaze Tracking Technique", ICPR 2000, vol. 4, pp. 201–204, 2000.

J. Liu et al., "Three–dimensional PC: toward novel forms of human–computer interaction", in Three–Dimensional Video and Display: Devices and Systems SPIE CR76, Nov. 5–8, 2000, Boston, MA, USA.

(List continued on next page.)

Primary Examiner—George Manuel
(74) Attorney, Agent, or Firm—Marc D. McSwain

(57) ABSTRACT

A system and method for eye gaze tracking without calibrated cameras, direct measurements of specific users' eye geometries, or requiring the user to visually track a cursor traversing a known trajectory. The preferred embodiment includes two uncalibrated cameras imaging the user's eye and having on-axis lighting. The cameras capture images of a test pattern in real space as reflected from the user's cornea, which is essentially a convex spherical mirror. The invention then extracts parameters required to define a mathematical mapping between real space and image space, including spherical and perspective transformations. The invention processes subsequent images of objects reflected from the user's eye through the inverse of the mathematical mapping to determine a gaze vector and a point of regard. Alternately, a single calibrated camera may be employed with means for estimating the eye-to-camera distance. A head-mounted embodiment that may include a laser pointer is also described.

15 Claims, 7 Drawing Sheets

OTHER PUBLICATIONS

Z. Zhang, "A Flexible New Technique for Camera Calibration", IEEE Transactions on Pattern Analysis and Machine Intelligence, vol. 22, No. 11, p1330–1334, 2000, also available as Technical Report MSR–TR–98–71, Microsoft Research, Microsoft Corporation, Redmond WA, http://research.microsoft.com/~zhang/Papers/TR98–71.pdf.

P. J. Kennedy, "Point of Regard Tracking Device", IBM Technical Disclosure Bulletin vol. 34, No. 10A, Mar. 1992.

Eye Movement Equipment Database (EMED), University of Darby, http://ibs.derby.ac.uk/emed.

Arnon Amir et al., "Calibration–Free Eye Gaze Tracking", U.S. Ser. No. 09/844,682.

* cited by examiner

SYSTEM AND METHOD FOR EYE GAZE TRACKING USING CORNEAL IMAGE MAPPING

CROSS-REFERENCE TO RELATED APPLICATIONS

This patent application is related to U.S. Ser. No. 09/844,682 "Calibration-Free Eye Gaze Tracking", a commonly-owned patent application filed on Apr. 27, 2001, which is hereby incorporated by reference. This patent application is also related to U.S. Ser. No. 09/238,979 "Method and Apparatus for Associating Pupils with Subjects", a commonly-owned patent application filed on Jan. 27, 1999, which is hereby incorporated by reference.

FIELD OF THE INVENTION

This invention relates to eye gaze tracking by analysis of images taken of a user's eye. The invention relates more specifically to eye gaze tracking without calibrated cameras, direct measurements of specific users' eye geometries, or requiring the user to visually track a cursor traversing a known trajectory.

BACKGROUND OF THE INVENTION

Eye gaze tracking technology has proven to be useful in many different fields, including human-computer interfaces for assisting disabled people interact with a computer. The eye gaze tracker can be used as an input device, instead of or in addition to a mouse for a personal computer, for example, helping disabled people to move a cursor on a display screen to control their environment and communicate messages. Gaze tracking can also be used for industrial control, aviation, and emergency room situations where both hands are needed for tasks other than operation of a computer but where an available computer is useful. There is also significant research interest in eye gaze tracking for babies and animals to better understand such subjects' behavior and visual processes.

There are many different schemes for detecting both the gaze direction and the point of regard, and many vendors of eye gaze tracking equipment (see for example web site http://ibs.derby.ac.uk/emed). Any particular eye gaze tracking technology should be relatively inexpensive, reliable, unobtrusive, easily learned and used and generally operator-friendly to be widely accepted. However, commercially available systems are expensive (over $10,000), complicated to install, and require a trained operator and a calibration process before each use session.

Corneal reflection eye gaze tracking systems project light toward the eye and monitor the angular difference between pupil position and the reflection of the light beam from the cornea surface. Near-infrared light is often employed, as users cannot see this light and are therefore not distracted by it. The light reflected from the eye has two major components. The first component is a 'glint', which is a very small and very bright virtual image of the light source reflected from the front surface of the corneal bulge of the eye; the glint is also known as the first Purkinje image. The second component is light that has entered the eye and has been reflected back out from the retina. This light serves to illuminate the pupil of the eye from behind, causing the pupil to appear as a bright disk against a darker background. This retroreflection, or "bright eye" effect familiar to flash photographers, provides a very high contrast image. An eye gaze tracking system determines the center of the pupil and the glint, and the change in the distance and direction between the two as the eye is rotated. The orientation of the eyeball can be inferred from the differential motion of the pupil center relative to the glint. The eye is often modeled as a sphere of about 12.3 mm radius having a spherical corneal bulge of about 7.4 mm radius (see "Schematic Eye" by Gullstrand, in *Visual Optics*, H. H. Emsley editor, $3^{rd}$ ed., p. 348, Butterworth, Scarborough, Ont., 1955, which is hereby incorporated by reference). The eyes of different users will have variations from these typical values, but individual dimensional values do not generally vary significantly in the short term, and thus can be stored and used for a long period.

As shown in prior art FIG. 1, the main components of a corneal reflection eye gaze tracking system include a video camera sensitive to near-infrared light, a near-infrared light source (often a light-emitting diode) typically mounted to shine along the optical axis of the camera, and a computer system for analyzing images captured by the camera. The on-axis light source is positioned at or near the focal center of the camera. Image processing techniques such as intensity thresholding and edge detection identify the glint and the pupil from the image captured by the camera using on-axis light, and locate the pupil center in the camera's field of view as shown in prior art FIG. 2.

Human eyes do not have uniform resolution over the entire field of view, nor is the portion of the retina providing the most distinct vision located precisely on the optical axis. The eye directs its gaze with great accuracy because the photoreceptors of the human retina are not uniformly distributed but instead show a pronounced density peak in a small region known as the fovea centralis. In this region, which subtends a visual angle of about one degree, the receptor density increases to about ten times the average density. The nervous system thus attempts to keep the image of the region of current interest centered accurately on the fovea as this gives the highest visual acuity. A distinction is made between the optical axis of the user's eye versus the foveal axis along which the most acute vision is achieved. As shown in prior art FIG. 3, the optical axis is a line going from the center of the spherical corneal bulge through the center of the pupil. The optical axis and foveal axis are offset in each eye by an inward horizontal angle of about five degrees, with a variation of about one and one half degrees in the population. The offsets of the foveal axes with respect to the optical axes of a user's eyes enable better stereoscopic vision of nearby objects. The offsets vary from one individual to the next, but individual offsets do not vary significantly in the short term. For this application, the gaze vector is defined as the optical axis of the eye. The gaze position or point of regard is defined as the intersection point of the gaze vector with the object being viewed (e.g. a point on a display screen some distance from the eye). Adjustments for the foveal axis offsets are typically made after determination of the gaze vector; a default offset angle value may be used unless values from a one-time measurement of a particular user's offset angles are available.

Unfortunately, calibration is required for all existing eye gaze tracking systems to establish the parameters describing the mapping of camera image coordinates to display screen coordinates. Different calibration and gaze direction calculation methods may be categorized by the actual physical measures they require. Some systems use physically-based explicit models that take into account eyeball radius, radius of curvature of the cornea, offset angle between the optical axis and the foveal axis, head and eye position in space, and distance between the center of the eyeball and the center of the pupil as measured for a particular user. Cameras may need to be calibrated as well, so that their precise positions and optical properties are known. Details of camera calibration are described in "A Flexible New Technique for Camera Calibration", Z. Zhang, IEEE Transactions on Pattern Analysis and Machine Intelligence, 22(11):1330–1334, 2000, (also available as Technical Report MSR-TR-98-71 at http://research.microsoft.com/~zhang/Papers/TR98-71.pdf), hereby incorporated by reference.

During system calibration, the user may be asked to fix his or her gaze upon certain "known" points in a display. At each coordinate location, a sample of corresponding gaze vectors is computed and used to accommodate head position, screen position and size, camera position, and to adapt the system to the specific properties of the user's eye, reducing the error in the estimate of the gaze vector to an acceptable level for subsequent operation. This method is disadvantageous in that a user's flow of thought is interrupted because the gaze target has nothing to do with the work the user wishes to perform. Further, the user may also be asked to click a mouse button after visually fixating on a target, but this approach may add synchronization problems, i.e. the user could look away from the target and then click the mouse button. Also, with this approach the system would get only one mouse click for each target, so there would be no chance to average out involuntary eye movements. System calibration may need to be performed on a per-user or per-tracking-session basis, depending on the precision and repeatability of the tracking system. A major disadvantage of the calibration process is that it requires the user's cooperation, and thus is unsuitable for infants, animals and for non-cooperative subjects.

U.S. Pat. No. 6,152,563 to Hutchinson et al. describes a typical corneal reflection eye gaze tracking system. The user looks at a sequence of fixed points on the screen to enable the system to map a particular glint-pupil displacement to a particular point on the screen. U.S. Pat. No. 5,231,674 to Cleveland et al. teaches another corneal reflection eye gaze tracking system.

U.S. Pat. No. 5,325,133 to Adachi teaches a method for eye gaze tracking in which the relative brightness of the pupil image as observed from multiple displacement angles determines a gaze vector. Alternate light source activation, or use of light sources of different wavelengths, correlates particular light sources with particular pupil images or pupil brightness measurements.

European Patent Application EP0631222A1, incorporated herein by reference, teaches a method of calculating the center position of a pupil image wherein the brightness of a gazing point on a display is increased, causing a change in pupil area subsequently used to verify the pupil image center position. This application also teaches the use of a simple linear relationship between screen coordinates (u,v) and pupil image center coordinates (x,y), $u=ax+b$ and $v=cy+d$, where parameters (a, b, c and d) are determined when pupil center position data is obtained at two locations.

U.S. Pat. No. 5,481,622 to Gerhardt et al. teaches a head-mounted eye-tracking system that constructs a mapping relationship between the relative position of the pupil image center position and the point of regard on a display screen. The user gazes at a cursor placed at a known position in a display screen, and the invention determines the pupil center position in image coordinates. This process is repeated many times, and a set of polynomial functions are eventually fitted to define the mapping relationship.

U.S. Pat. Nos. 5,231,674, 5,325,133, 5,481,622, 6,152,563 are all incorporated herein by reference.

While the aforementioned prior art methods are useful advances in the field of eye gaze tracking, systems that do not require user-apparent calibration would increase user convenience and broaden the acceptance of eye gaze tracking technology. A system for eye gaze tracking without calibrated cameras, direct measurements of specific users' eye geometries, or requiring the user to visually track a cursor traversing a known trajectory is therefore needed.

SUMMARY OF THE INVENTION

It is accordingly an object of this invention to devise a system and method for eye gaze tracking wherein calibrated cameras and direct measurement of individual users' eye geometries are not required.

It is a related object of the invention to devise a system and method for eye gaze tracking wherein the user is not required to fixate on a series of visual targets located at known positions, or to visually track a cursor traversing a known trajectory.

It is a related object of the invention to determine a gaze vector and to compute a point of regard, which is the intersection of the gaze vector and an observed object. The observed object is preferably a display screen or computer monitor, but may also include a desktop, a windshield, a whiteboard, an advertisement, a television screen, or any other object over which a user's vision may roam.

It is a related object of the preferred embodiment of the invention that two cameras are used to capture images of a user's eye, where each camera includes an on-axis light source, a focal center, and an image plane defining an image coordinate system. It is a related object of the preferred embodiment of the invention to capture images of a user's eye such that the pupil center in each image and a glint resulting from the particular camera's light source may be readily identified and located in the image plane of each camera.

It is a related object of the preferred embodiment of the invention that the cameras capture images of a set of reference points, or a test pattern, that defines a reference coordinate system in real space. The images include reflections of the test pattern from the user's cornea, which is essentially a convex spherical mirror. The invention maps or mathematically relates the test pattern image in the camera image coordinate systems to the actual test pattern through spherical and perspective transformations. The parameters of the relation may include the eye-to-camera distance, the vertical and horizontal displacement of the eye from the test pattern, and the radius of cornea curvature.

The test pattern may comprise an unobtrusively interlaced pattern depicted in a display screen, a set of light sources around a display screen border that may be sequentially activated, a printed pattern around the display screen, a set of light sources placed on the display screen surface, or any other distinctive pattern not attached to the display screen but within the user's view of the display screen vicinity. The test pattern is preferably invisible or not obtrusive to the user. The test pattern is preferably coplanar with the surface the user is viewing, but is not constrained as such, i.e. there may be separate reference and target coordinate systems sharing a known mapping relationship. The cameras are preferably positioned in the plane of the test pattern, and may for example be built into a computer display screen. Cameras may be attached to a head mounted device, such as a helmet or glasses. Alternately, the cameras may be positioned away from the reference plane and the plane of the user-viewed surface.

Once the invention defines the mapping between the reference coordinate system and the image coordinate system, the invention applies the mapping to subsequent images reflected from the user's cornea. The glint from the on-axis light source, the focal center of the camera, and the pupil center define a plane in real space that intersects with a user-viewed planar surface along a line. This line contains the point of regard T, which lies between the glint and the pupil center as mapped onto the screen coordinate system. The line also contains point V, where a virtual light source would produce a glint at the pupil center of the reflected corneal image as seen by the camera. The gaze vector is the bisector of the angle between the focal center of the camera, the pupil center in real space, and point V.

The invention uses the mapping relationship already determined via the test pattern to compute where a virtual light source would have to be on the user-viewed surface to create a reference point in the pupil center in the camera image coordinate system. If uncalibrated cameras are used, two cameras are required to uniquely determine the point of regard T. If one calibrated camera is used, the distance from the camera's focal center to the user's pupil needs to be known or estimated; the focal length of the camera and an estimate of the distance between the user's eyes can be used to estimate eye-to-camera distance.

The invention may also interpolate the location of points T or V from a test pattern around the perimeter of the display screen, including the mapping described above. At least one of the cameras may be head-mounted. A laser pointer can generate additional reference points, and can be actively aimed to establish a reference point at point V for example. Correction for foveal axis offsets may be added.

The foregoing objects are believed to be satisfied by the embodiments of the present invention as described below.

DETAILED DESCRIPTION OF THE INVENTION

Figure 1:
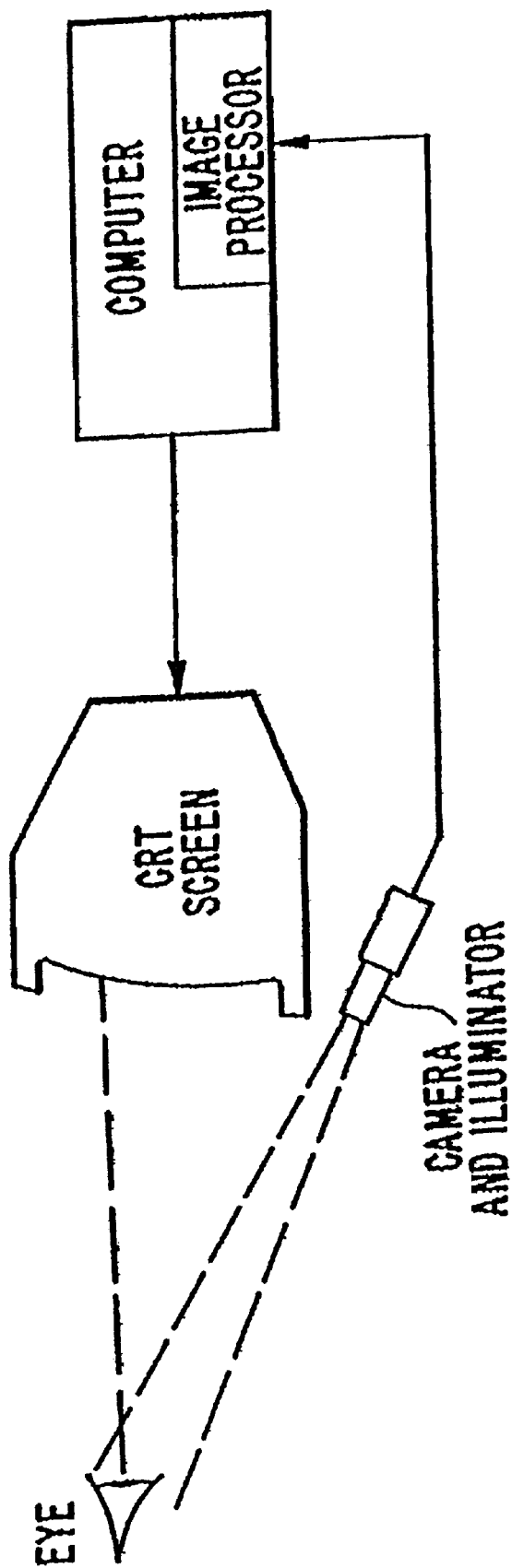
FIG. 1 is a prior art diagram of an eye gaze tracking system.
Figure 2:
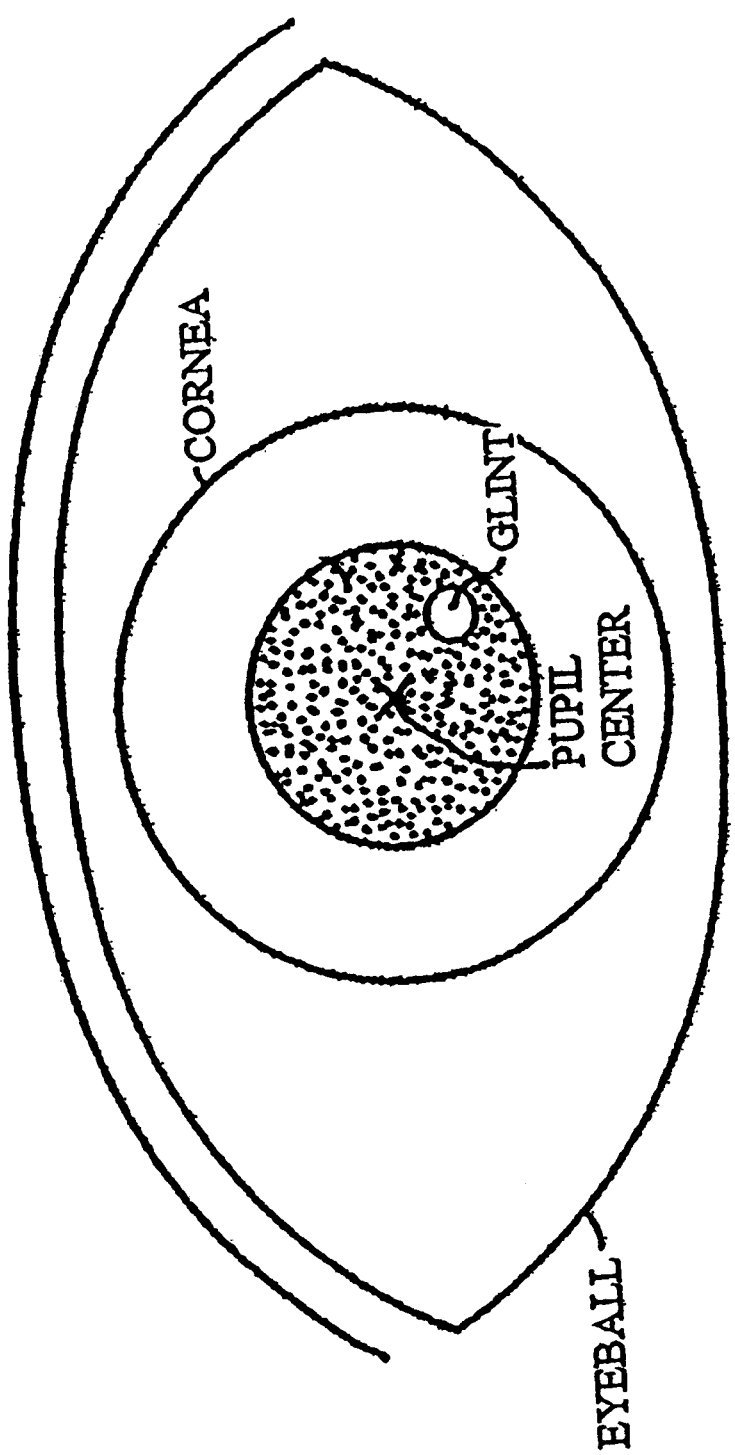
FIG. 2 is a prior art diagram of a user's eye as viewed by a camera.
Figure 3:
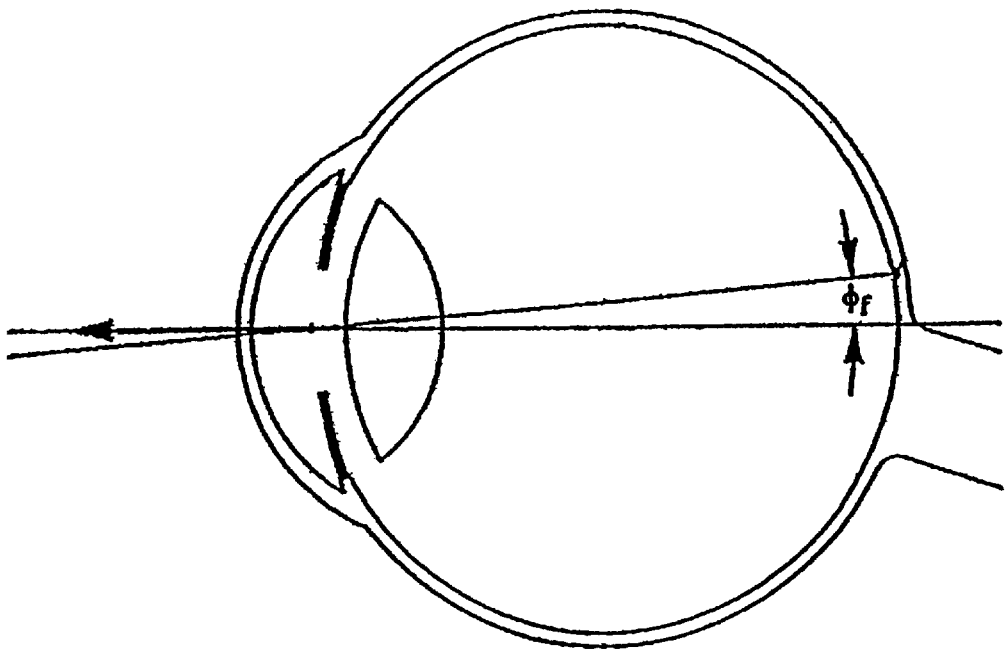
FIG. 3 is a prior art diagram of the foveal and optical axes and their offset angle.
Figure 3:
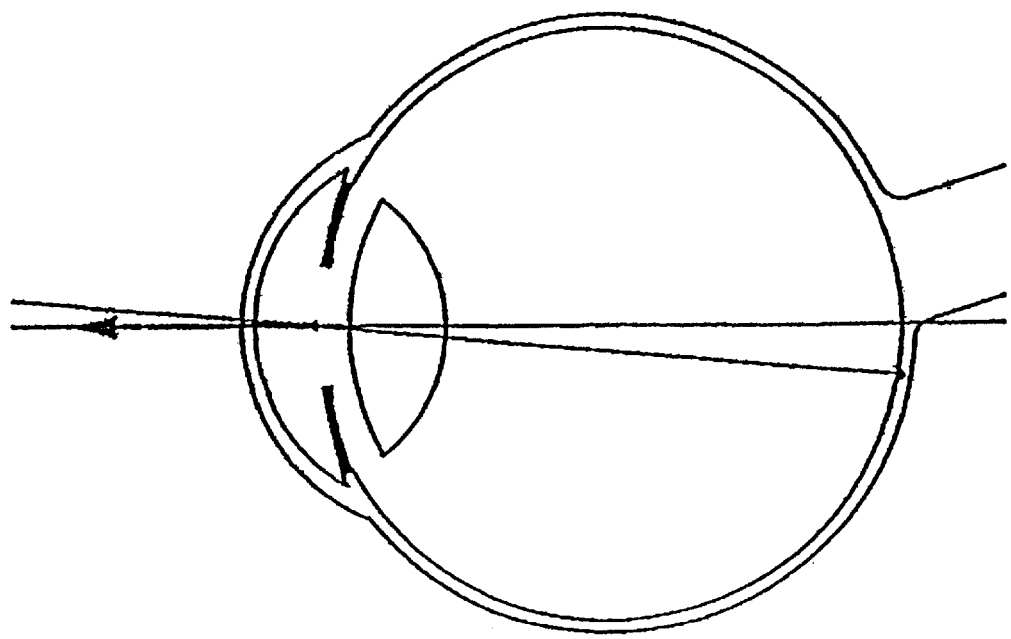
Figure 4:
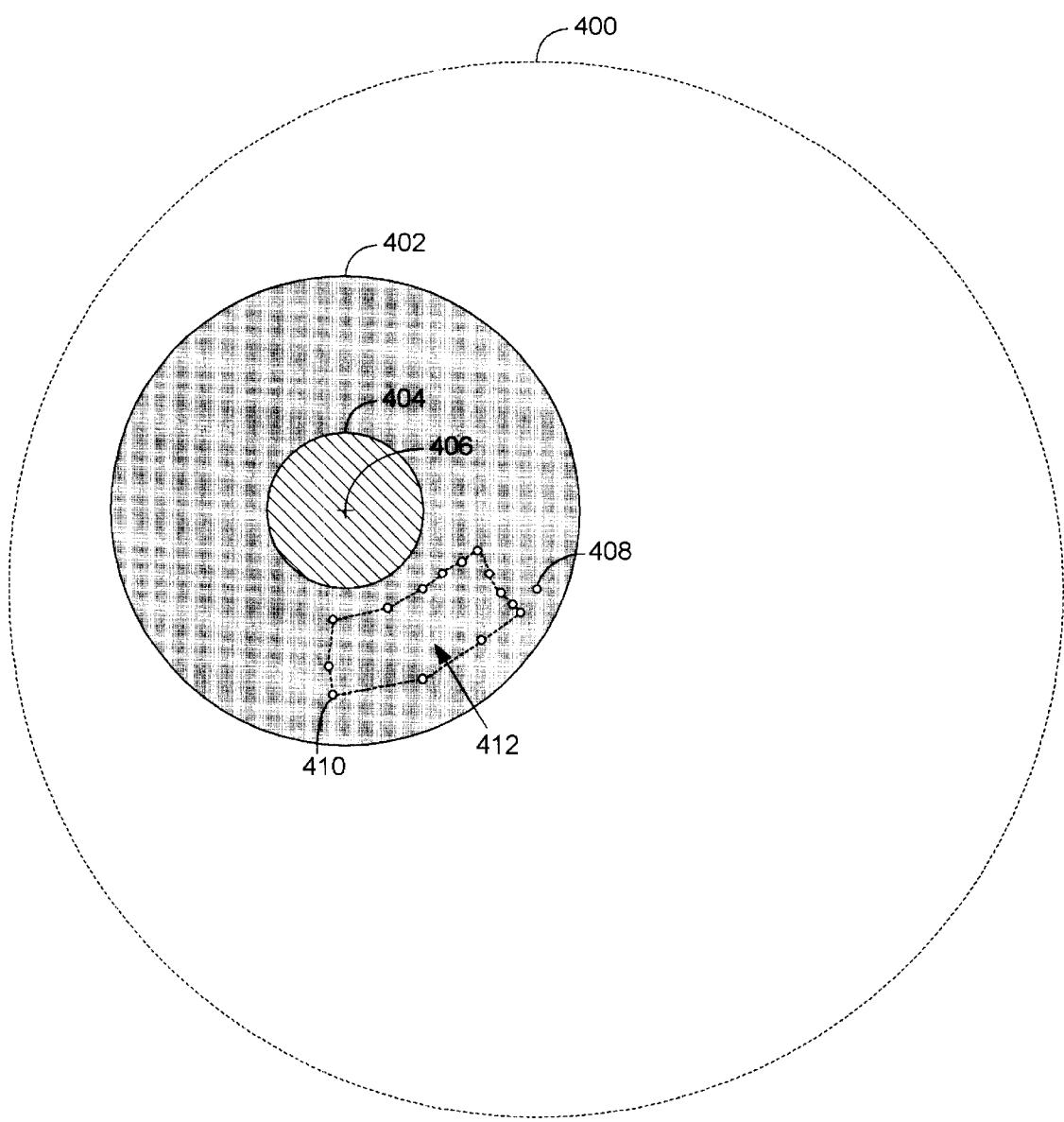
FIG. 4 is a diagram of the user's eye according to the preferred embodiment of the present invention.

Referring now to FIG. 4, a diagram of user's eye 400 according to the preferred embodiment of the present invention is shown. The user's eye 400 includes the eyeball or sclera, a substantially spherical cornea 402, and a pupil 404 having a pupil center 406. Note that non-spherical cornea models, including parabolic models, are known in the art and can also be employed by the present invention. At least one camera (not shown) captures images of user's eye 400, particularly cornea 402. FIG. 4 is such an image. Cameras may be head-mounted for easy acquisition of an eye image, but are preferably not head-mounted so the invention will be more widely accepted by users. The cameras track the user's head motion using known techniques. Each camera includes a focal center, an on-axis light source illuminating the eye, and an image plane defining an image coordinate system. The light source is preferably invisible to prevent user distraction, and may for example emit radiation in the near-infrared wavelength range. The images of user's eye 400 include image aspects that will be used for determination of an eye gaze vector and determination of a point of regard, which is the intersection of the gaze vector and an observed object. These image aspects include a glint 408 due to light from the on-axis light source reflecting from eye 400 (either sclera or cornea 402) directly back to the camera. (pupil center 406 may be offset slightly due to refraction through cornea 402; the offset can be computed by the present invention, using an estimate of the index of refraction and the distance of pupil 404 behind cornea 402 according to the Gullstrand eye model.) The image aspects also include a pupil image preferably created via retroreflection as is known in the art. Various image processing methods for identifying and locating the center of glint 408, pupil 404, and pupil center 406 in captured images of user's eye 400 are known in the art.

The image aspects also include a reflected version of a set of reference points 410 forming a test pattern 412. Reference points 410 define a reference coordinate system in real space. The relative positions of reference points 410 to each other are known, and reference points 410 are preferably co-planar, although that is not a limitation of the present invention. The reflection of reference points 410 is spherically distorted by reflection from cornea 402, which serves essentially as a convex spherical mirror. The reflected version of reference points 410 is also distorted by perspective, as eye 400 is some distance from the camera and the reflected version goes through a perspective projection to the image plane. That is, test pattern 412 will be smaller in the image plane when eye 400 is farther away from reference points 410. The reflection also varies in appearance due to the radius of cornea curvature, and the vertical and horizontal translation of user's eye 400.

There are many possible ways of defining the set of reference points 410 or test pattern 412. Test pattern 412 is preferably generated by a set of point light sources deployed around a display screen perimeter. If necessary, the light sources can be sequentially activated to enable easier identification of which light source corresponds to which image aspect. For example, a set of lights along one vertical edge of the display screen may be activated during acquisition of one image, then a set of lights along one horizontal edge of the display screen, and so forth. A variety of different lighting sequences and patterns can be used. The light sources can be built into a computer monitor during manufacture or subsequently attached to the screen, and preferably emit infrared light. Alternately, test pattern 412 may comprise an unobtrusively interlaced design depicted in a display screen; in this case no separate light sources are needed, but the camera is preferably synchronized to acquire an image of test pattern 412 reflection when the design is being displayed. A set of light sources on the display screen itself can also generate test pattern 412; for example, pixels in a liquid crystal display may include an infrared-emitting device such as a light-emitting diode. It is known in the art that red liquid crystal display cells are at least partially transparent to infrared light. Another method for defining test pattern 412 is to deploy a high-contrast pre-printed pattern around the display screen perimeter; a checkerboard pattern for example.

In yet another variation, the regularly depicted display screen content can itself serve as test pattern 412. The content can be fetched from video memory or a display adapter (not shown) to allow matching between the displayed content and image aspects. If a high frame rate camera is used, camera frames may be taken at a different frequency (e.g. twice the frequency) than the display screen refresh frequency, thus frames are captured in which the screen reflection changes over time. This allows easier separation of the screen reflection from the pupil image, e.g. by mere subtraction of consecutive frames. Generally, any distinctive pattern within the user's view can comprise test pattern 412, even if not attached to the display screen or other object being viewed.

In the examples above, test pattern 412 is usually co-planar with the surface being viewed by the user, such as a computer monitor or display screen, but the present invention is not constrained as such. The reference coordinate system may not necessarily coincide with a coordinate system describing the target on which a point of regard exists, such as the x-y coordinates of a computer monitor. As long as a mapping between the reference coordinate system and the target coordinate system exists, the present invention can compute the point of regard. Other target objects could include but are not limited to a desktop, a whiteboard, and a windshield. The camera is preferably positioned in the plane of reference points 410, but the present invention is not limited to this embodiment, as will be described below.

The present invention mathematically maps the reference coordinate system to the image coordinate system by determining the specific spherical and perspective transformations that cause reference points 410 to appear at specific relative positions in the reflected version of test pattern 412. The invention updates the mathematical mapping as needed to correct for changes in the position or orientation of user's eye 400, but this updating is not necessarily required during every cycle of image capture and processing. The invention then applies the mathematical mapping to image aspects other than reflected reference points 410, such as glint 408 and pupil center 406, as will be described below.

Figure 5:
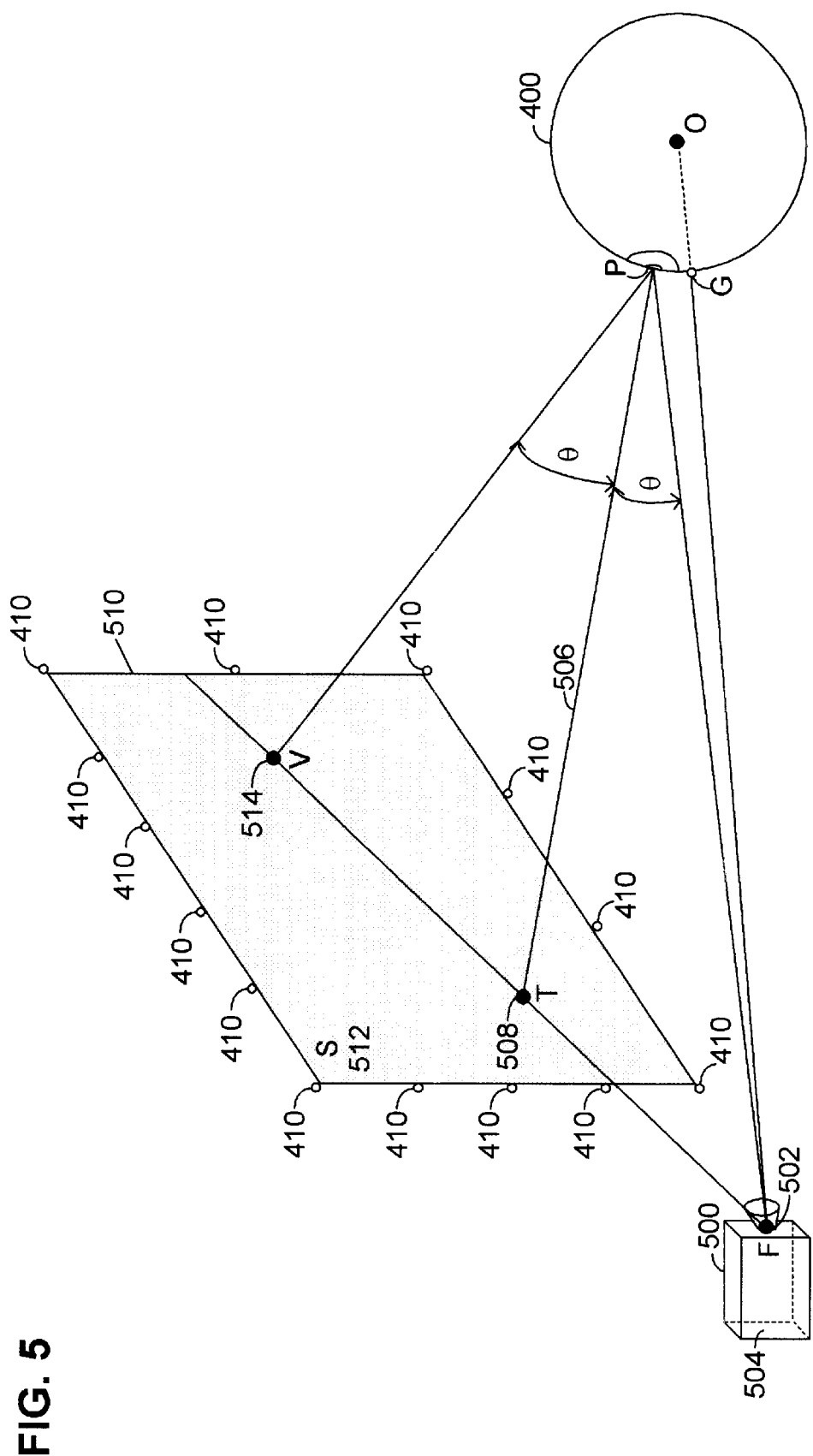
FIG. 5 is a diagram of the user's eye with regard to a camera located in a screen plane according to the preferred embodiment of the present invention.

Referring now to FIG. 5, a diagram of user's eye 400 with regard to a camera located in a screen plane according to the preferred embodiment of the present invention is shown. Camera 500 includes a focal center 502, an image plane 504 that defines an image coordinate system, and an on-axis light source (not shown). The center of user's eye 400 is designated as point O. The reflection point of the on-axis light source from user's eye 400 is designated as point G, which is seen by camera 500 as glint 408 as shown in FIG. 4. The center of the pupil is designated as point P in real space, and is seen by camera 500 as pupil center 406 in image coordinates. Gaze vector 506 is the line extending from point P to the specific location (point T) on an object being directly observed by a user. Point of regard 508 is thus the intersection of gaze vector 506 with an observed object, and in this description the observed object is a display screen 510 as typically employed with a computer. Display screen 510 is preferably modeled as plane S, which is screen plane 512. While the observed object is preferably planar, the invention is not limited to gaze tracking on planar objects, as will be described further below. Point V is the position of a virtual light source 514 that, if it actually existed at point V, its reflection from user's eye 400 would appear to coincide with pupil center 406 in image plane 504 of camera 500. Or, going the other way, point V is the location of the pupil center 406 when mapped from image coordinates to screen plane coordinates. Points F, P, G, O, T, and V as shown in FIG. 5 are all co-planar. Points F, T, and V lie on a line that is co-planar with screen plane S. Angle FPT and angle VPT are equal; in other words, gaze vector 506 bisects angle FPV.

The preferred embodiment of the invention employs at least one camera 500 co-planar with screen plane 512 to capture an image of reference points as reflected from cornea 402. Specific reference points may be identified by many different means, including alternate timing of light source energization as well as matching of specific reference point distribution patterns. The invention then determines the specific spherical and perspective transformations required to best map the reference points in real space to the test pattern they form in image space. The invention can for example optimize mapping variables (listed above) to minimize the difference between the observed test pattern in image coordinates and the results of transforming a known set of reference points in real space into an expected test pattern in image coordinates. Once the mathematical mapping between the image coordinate system and the reference coordinate system is defined, the invention applies the mapping to observed image aspects, such as backlighted pupil images and the glint due to the on-axis light source. The invention can compute the location of point V in the coordinates of the observed object (screen plane 512) by locating pupil center 406 in image coordinates and then mathematically converting that location to coordinates within screen plane 512. Similarly, the invention can compute the location of glint 408 in image coordinates and determine a corresponding location in the coordinates of the observed object; in the case where camera 500 is co-planar with screen plane 512, the mapped glint point is simply focal center 502. Point of regard 508 on screen plane 512 is typically the bisector of a line segment between point V and such a mapped glint point. Glint 408 and pupil center 406 can be connected by a line in image coordinates and then reference point images that lie near the line can be selected for interpolation and mapping into the coordinates of the observed object.

A single calibrated camera 500 can determine point V and bisection of angle FPV determines gaze vector 506; if the eye-to-camera distance FP is known then the intersection of gaze vector 506 with screen plane 512 can be computed and determines point of regard 508. The eye-to-camera distance can be measured or estimated in many different ways, including the distance setting at which camera 500 yields a focused image, the scale of an object in image plane 504 as seen by a lens of known focal length, or via use of an infrared rangefinder.

The present invention can also employ uncalibrated cameras 500 for gaze tracking, which is a significant advantage over existing gaze tracking systems. Each uncalibrated camera 500 can determine a line on screen plane 512 containing point of regard 508, and the intersection of two such lines determines point of regard 508. Mere determination of a line that contains point of regard 508 is of use in many situations, as described in U.S. Ser. No. 09/844,682 cited previously.

When non-planar objects are being viewed, the intersection of the object with plane FPV is generally a curve instead of a line, and the method of computing gaze vector 506 by bisection of angle FPV will yield only approximate results. However, these results are still useful if the object being observed is not too strongly curved, or if the curvature is included in the mathematical mapping.

An alternate embodiment of the present invention employs a laser pointer to create at least one reference point.

The laser pointer can be scanned to produce a test pattern on objects in real space, so that reference points need not be placed on observed objects a priori. Alternately, the laser pointer can be actively aimed, so that the laser pointer puts a spot at point V described above (i.e. a reflection of the laser spot is positioned at pupil center 406 in the image coordinate system). The laser may emit infrared or visible light.

Gaze vector 506, however determined, can control a laser pointer such that a laser spot appears at point of regard 508. As the user observes different objects and point of regard 508 changes, the laser pointer follows the motion of the point of regard so that user eye motion can be observed directly in real space.

Figure 6:
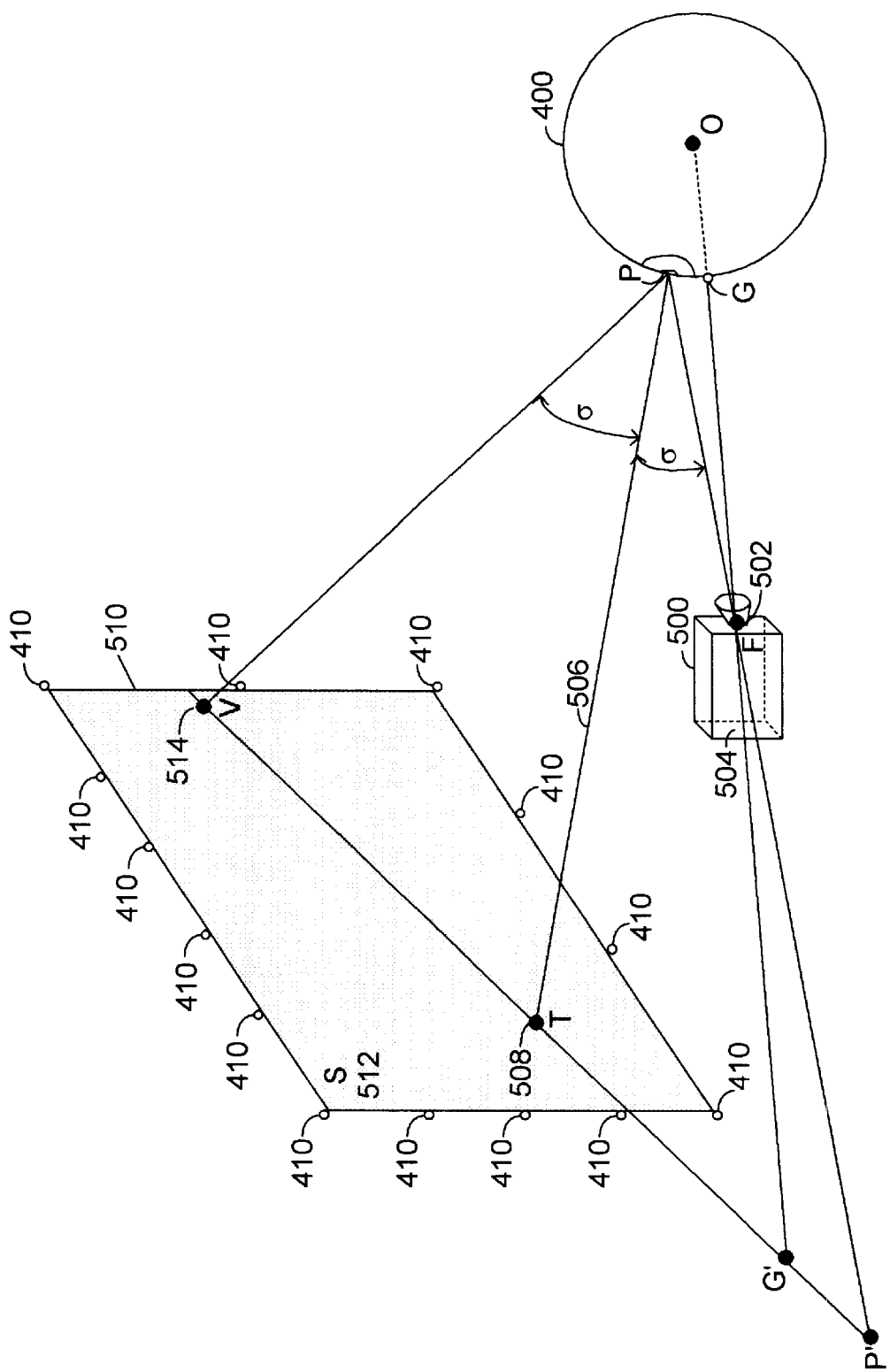
FIG. 6 is a diagram of the user's eye with regard to a camera located out of the screen plane according to the preferred embodiment of the present invention.

Referring now to FIG. 6, a diagram of user's eye 400 with regard to a camera 500 located out of the screen plane according to the preferred embodiment of the present invention is shown. Although focal center 502 is no longer co-planar with screen plane 512, the images of glint 408 and pupil center 406 can be effectively projected back mathematically as points P' and G' on a line that is co-planar with screen plane 512. Point T is on the line connecting point G' with point V, as previously described.

Figure 7:
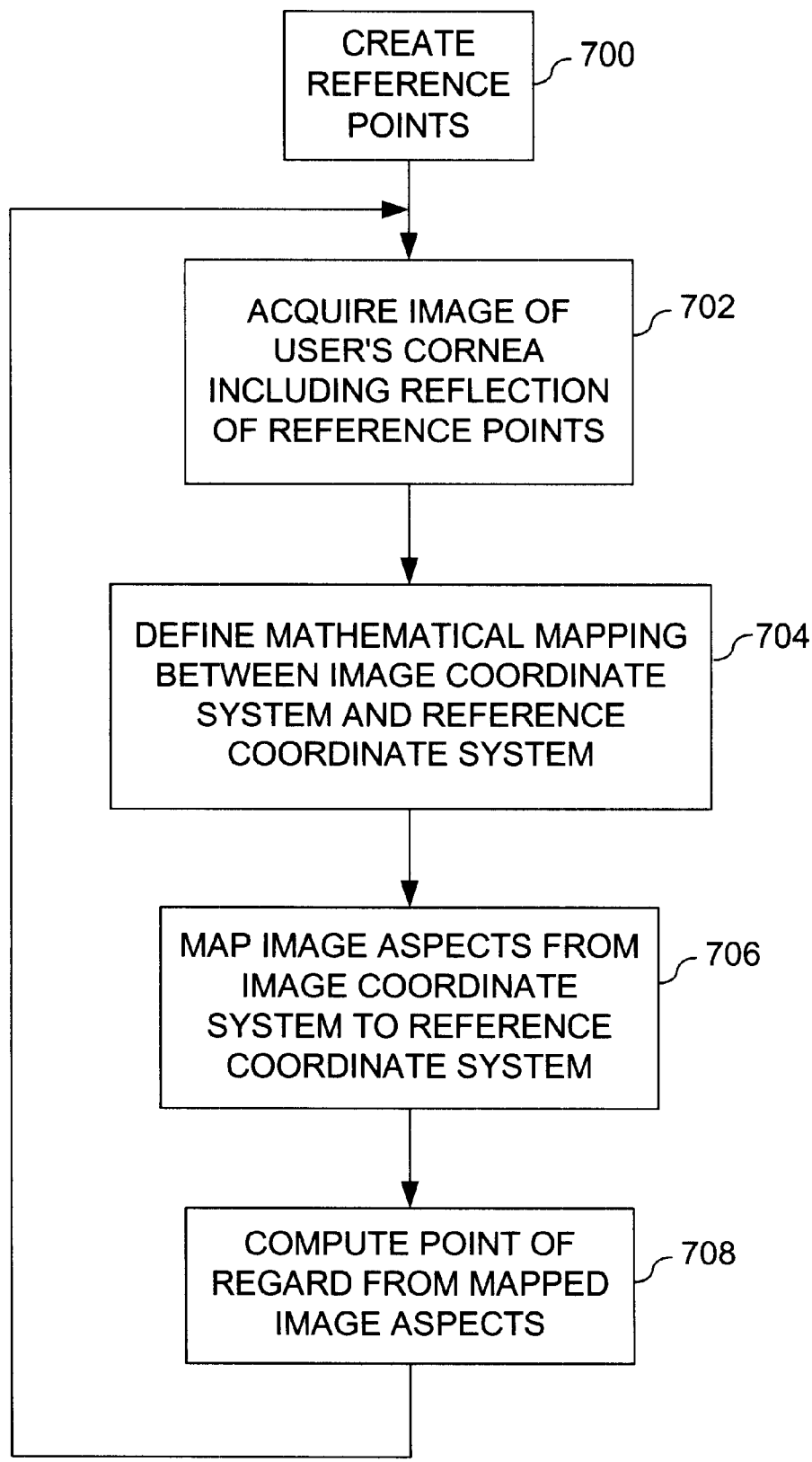
FIG. 7 is a flowchart of the eye gaze tracking method according to the preferred embodiment of the present invention.

Referring now to FIG. 7, a flowchart of the eye gaze tracking method according to the preferred embodiment of the present invention is shown. In step 700, reference points 410 as described above are created or activated. Next, in step 702 the invention acquires at least one image of cornea 402 including reflections of reference points 410. In step 704, the invention defines a mathematical mapping between the image coordinate system and the reference coordinate system by determining the transformations (e.g. spherical and perspective) that cause reference points 410 as distributed in the image coordinate system to best fit their expected positions based on their known distribution in the reference coordinate system. The invention then maps image aspects such as glint 408 and pupil center 406 from the image coordinate system to the reference coordinate system in step 706. Finally, the invention computes the point of regard from the mapped image aspects in step 708, and returns to step 702 to repeat the eye gaze tracking method steps described. Note that steps 702 and 704 need not necessarily be performed during every single execution cycle of the method; it is within the scope of the invention that the mapping of coordinate systems by analysis of reflected reference points 410 may be performed only occasionally so the invention spends most of its time mapping image aspects other than reference points 410 and tracking the point of regard as described in steps 706 and 708.

A general purpose computer is programmed according to the inventive steps herein. The invention can also be embodied as an article of manufacture—a machine component—that is used by a digital processing apparatus to execute the present logic. This invention is realized in a critical machine component that causes a digital processing apparatus to perform the inventive method steps herein. The invention may be embodied by a computer program that is executed by a processor within a computer as a series of computer-executable instructions. These instructions may reside, for example, in RAM of a computer or on a hard drive or optical drive of the computer, or the instructions may be stored on a DASD array, magnetic tape, electronic readonly memory, or other appropriate data storage device.

While the invention has been described with respect to illustrative embodiments thereof, it will be understood that various changes may be made in the apparatus and means herein described without departing from the scope and teaching of the invention. Accordingly, the described embodiment is to be considered merely exemplary and the invention is not to be limited except as specified in the attached claims.

We claim:

1. A method for eye gaze tracking, comprising the steps of:
   creating a set of reference points in a reference coordinate system;
   acquiring at least one image of at least one of a user's corneas, said image having image aspects in an image coordinate system and including reflections of said reference points;
   defining a mathematical relationship between said reference coordinate system and said image coordinate system;
   mapping said image aspects from said image coordinate system to said reference coordinate system using said mathematical relationship; and
   computing a point of regard from said mapped image aspects.

2. The method of claim 1 wherein said reference points include at least one of: a printed pattern around a screen, an unobtrusively interlaced pattern in said screen, a set of controlled light sources around said screen, a set of controlled light sources on said screen, content displayed in said screen, a set of controlled light sources behind said screen.

3. The method of claim 2 wherein said screen includes at least one of: a computer monitor, a whiteboard, a desktop, a windshield, an advertisement, a television screen.

4. The method of claim 1 wherein a laser pointer creates at least one new reference point.

5. The method of claim 4 wherein said laser pointer creates said new reference point that reflects from said cornea at a pupil image center in said image coordinate system.

6. The method of claim 1 wherein said acquiring step is performed by at least one camera focusing upon at least one of said user's corneas, each said camera having a focal center, an image plane defining said image coordinate system, and an on-axis light source.

7. The method of claim 6 wherein said image aspects are identified by subtracting a number of said images acquired during different phases of display screen refresh cycles.

8. The method of claim 6 comprising the further steps of:
   determining for each of said cameras an angle between said focal center, a user's pupil center, and a point on a predetermined target surface where a virtual light source would create a new image aspect at a pupil image center in said image coordinate system; and
   defining a gaze vector as the bisector of said angle.

9. The method of claim 8 comprising the further step of correcting said gaze vector for a foveal axis offset angle.

10. The method of claim 6 wherein at least one of said cameras is head-mounted.

11. The method of claim 1 wherein said mathematical relationship includes at least one of: spherical transformations, perspective transformations, polynomial interpolation.

12. The method of claim 1 wherein said computing step includes the further steps of:
   mapping a target coordinate system to said reference coordinate system; and
   bisecting a line segment spanning an on-axis glint and a pupil image center in said target coordinate system.

13. The method of claim 12 wherein said target coordinate system is said reference coordinate system.

14. A system for eye gaze tracking comprising:
   means for creating a set of reference points in a reference coordinate system;
   means for acquiring at least one image of at least one of a user's corneas, said image having image aspects in an image coordinate system and including reflections of said reference points;
   means for defining a mathematical relationship between said reference coordinate system and said image coordinate system;
   means for mapping said image aspects from said image coordinate system to said reference coordinate system using said mathematical relationship; and
   means for computing a point of regard from said mapped image aspects.

15. A computer program product including a program storage device readable by a machine, tangibly embodying a program of instructions executable by the machine to perform method steps for eye gaze tracking, said program comprising:

a first code means for creating a set of reference points in a reference coordinate system;

a second code means for acquiring at least one image of at least one of a user's corneas, said image having image aspects in an image coordinate system and including reflections of said reference points;

a third code means for defining a mathematical relationship between said reference coordinate system and said image coordinate system;

a fourth code means for mapping said image aspects from said image coordinate system to said reference coordinate system using said mathematical relationship; and a fifth code means for computing a point of regard from said mapped image aspects.

* * * * *